United States Patent [19]

Larm et al.

[11] Patent Number: 4,795,745

[45] Date of Patent: Jan. 3, 1989

[54] MACROPHAGE-ACTIVATING COMPOSITION AND A PROCESS FOR ITS MANUFACTURE

[76] Inventors: Karl O. P. Larm, Medicarb AB, 113 47 Stockholm; James Hoffman, Sveriges Lantbruksuniversitet, Inst. Kemi, 750 07 Uppsala, both of Sweden; Rolf Seljelid; Jarl Bøgwald, both of Institutt for Medisinsk Biologi, Post Boks 977, 9001 Tromsø, Norway

[21] Appl. No.: 777,527

[22] Filed: Sep. 19, 1985

[30] Foreign Application Priority Data

Sep. 19, 1984 [SE] Sweden ................................ 8404699

[51] Int. Cl.⁴ .......................................... A61K 37/715
[52] U.S. Cl. .......................................... 514/54; 536/1.1
[58] Field of Search ..................... 514/54, 56; 536/1.1, 536/17.2, 18.7, 21, 114, 123

[56] References Cited

U.S. PATENT DOCUMENTS 4,156,066  5/1979  Gould ................................... 528/73
4,414,325 11/1983  Masuda ................................. 435/7

OTHER PUBLICATIONS

Glycan Stimulation of Macrophages In Vitro, R. Seljelid, G. Bogwald and A. Lundwall, Experimental Cell Research 131 (1981) 121 to 129.

Primary Examiner—Matthew A. Thexton
Assistant Examiner—Catherine S. Kilby
Attorney, Agent, or Firm—Burns, Doane, Swecker & Mathis

[57] ABSTRACT

Macrophage-stimulatory composition containing a water-soluble β-1.3-bound glucan and a water-insoluble carrier to which the glucan has been immobilized; its use; and a process for its manufacture.

8 Claims, 1 Drawing Sheet

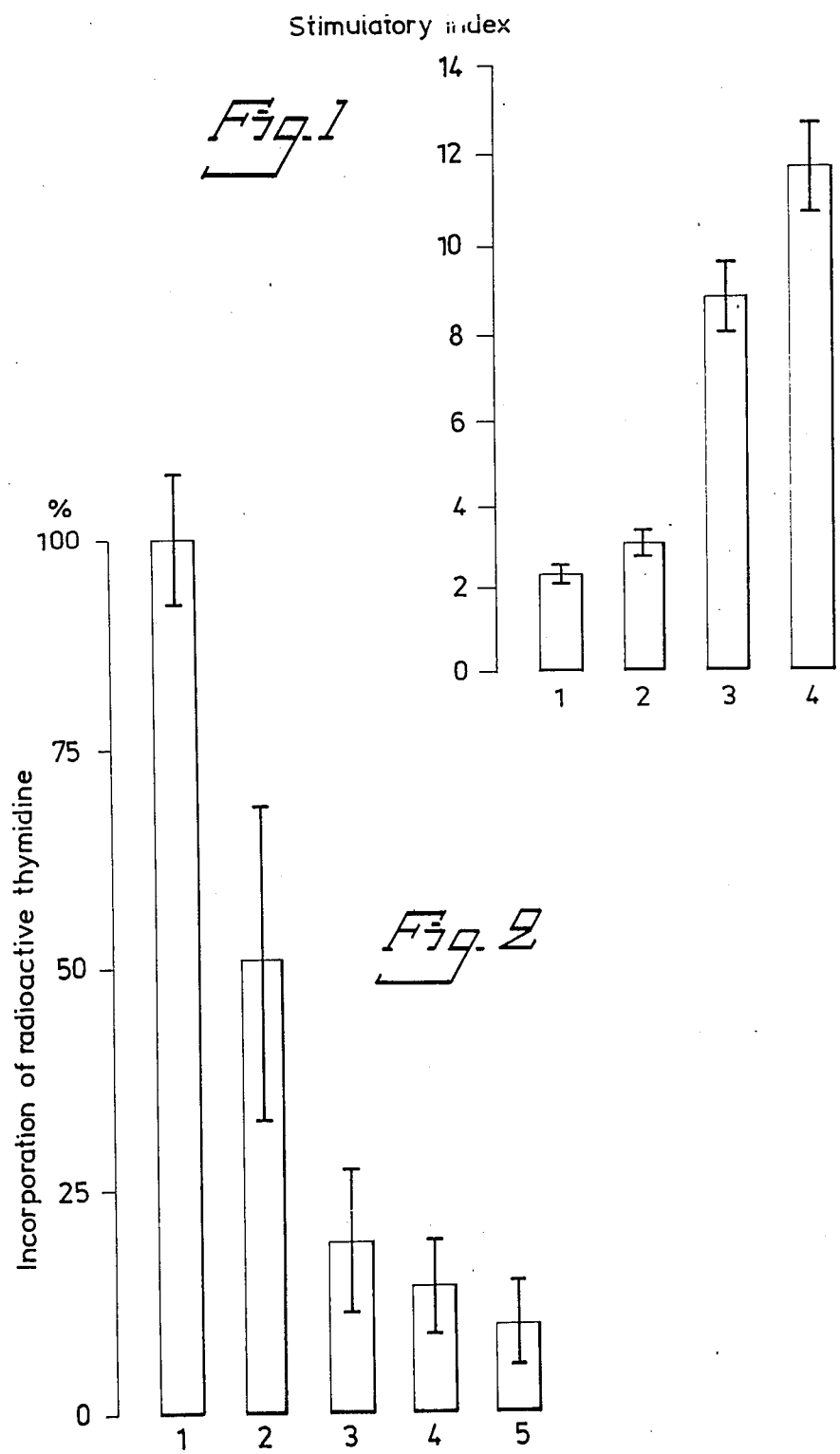

MACROPHAGE-ACTIVATING COMPOSITION AND A PROCESS FOR ITS MANUFACTURE

The present invention relates to a macrophage-activating composition containing a water-soluble β-1.3-bound D-glucan and a water-insoluble carrier to which said glucan is immobilized. A water-soluble glucan immobilized in this manner has in connection with the invention been found to possess capability of activating mononuclear phagocytes, so called macrophages.

It is known that certain polysaccharides improve the defence mechanism of the body, i.a. through activation of the complement system and stimulation of the function of monocytes-macrophages. These cells are of a central importance to the defense of the body, both from the inside and from the outside, for example against the growth of cancer cells or the attack of for example bacteria.

It has been previously shown (GLYCAN STIMULATION OF MACROPHAGES IN VITRO, R. Seljelid, G. Bögwald and Å. Lundwall, Experimental Cell Research 131 (1981) 121 to 129), that certain and necessarily non-soluble glucans, particularly such containing 1.3-bound β-D-glucose entities, activate macrophages in vitro and make same cytotoxic.

Since insoluble compounds often are unsuitable to use in vitro and in vivo the main object of the invention is to provide a composition having the ability of providing activation of macrophages making it possible to obtain controlled conditions.

Another object of the invention is to provide a process for the manufacture of such composition.

In accordance with the present invention it has been suprisingly found that water-soluble β-1.3-bound D-glucans which normally do not activate macrophages by immobilization to a water-insoluble carrier obtain macrophage-stimulating properties. Soluble, per se inactive β-1.3-bound D-glucans thus activate macrophages after immobilization to suitable surfaces. Such surfaces find broad utility in medicinal technology. As examples there may be mentioned different forms of extracorporeal circulation, where blood is passed over surfaces coated with β-1.3-bound D-glucans. Other medicinal applications are presented in the following in the exemplifying part of the disclosure.

As examples of β-1.3-bound D-glucans useful in the present invention there may be mentioned laminaran, curdlan, pachyman, yeast glucan and lichenan.

By the expression "macrophage" as used in the present disclosure is meant mononuclear phagocytes which is a more adequate expression from a scientific point of view.

The technique according to the present invention may thus primarily be used for activating mononuclear phagocytes of animals including man. This means that the composition according to the present invention can be used for improving the body defense of animals, for example against infections and cancer, particularly humans and commercially useful animals. Such conceivable areas of use are verified by the experimental tests which are presented in the following in the present disclosure.

The immobilization of the glucan is preferably provided by covalent coupling to a suitable carrier. Particularly preferred is the use of carriers containing amino groups to which the glucan is coupled. The preferred technique thus means that the surface of the carrier is first activated by introduction of amino groups. The glucan is modified in such a manner as to be covalently bindable to the aminated surface. The character of the carrier is not critical and the use of different types of plastics is conceivable as well as the use of aminated gels.

The technique for covalent coupling of a glucan to a surface while using binding to amine groups is, as previously indicated, a preferred technique for immobilization. As example a β-1.3-bound D-glucan is degraded in a suitable acid, preferably a strong acid, for example formic acid, and is then treated with 2-chloracetaldehydodimethylacetal for substitution with O-(2.2'-dimetoxyethyl)-groups. Such substituted glucan is then treated with acid to form aldehyde groups, the aldehyde-substituted glucan being then brought into contact with a carrier containing amino groups in the presence of cyanoborohydride, covalent coupling to the carrier being provided. In another example epoxy functions are introduced in a glucan by activation with epichlorohydrin. When the epoxy-activated glucan is brought into contact with a carrier containing amino groups these latter react with the epoxy groups, the glucan being covalently bound to the carrier. Details concerning the coupling technique is clear from the following specific examples.

Reverting to the application of the invention it has been found that in accordance with the invention immobilized β-1.3-bound D-glucans show cytostatic effect and antibacterial effect. The fact that immobilized β-1.3-bound D-glucans activate macrophages so that they provide for a cytostatic effect is shown in the present disclosure by the use of tumor cells and macrophages in culture on tissue cultivating plates covered with β-1.3-bound D-glucans. The results are presented below in the examples.

The fact that immobilized β-1.3-bound macrophages possess antibacterial activity is shown in the disclosure by the fact that β-1.3-bound D-glucans coupled to polystyrene spheres prevent peritonite in mice infected with pneumococci or streptococci. The results in connection hereto are unambiguous in that all test animals in the control group died, whereas all animals treated with glucan-coated polystyrene spheres survived.

The invention also provides for a macrophage-stimulatory composition containing as an active constituent an immobilized glucan according to the invention in combination with a pharmaceutically acceptable carrier.

The active immobilized glucans according to the present invention can, in a conventional manner, be formulated for use in human or veterinary medicine. The composition or the pharmaceutical preparation can contain the active constituents in combination with a pharmaceutically acceptable carrier which may be solid, semi-solid or liquid depending on the route of administration and other actual conditions. Sometimes it may also be suitable to use a bio-degradable carrier. The active constituents may also be used as such without the addition of carrier materials. The compositions are manufactured in full conformity with conventional pharmaceutical practice.

As previously indicated the function of the mononuclear phagocytes is of a central importance to the defense of the body both in influence from the inside and from the outside. Through the present invention compositions are made available which have the ability of generally activating the defense system of the body, for example against growth of cancer cells, infections etc. Such applications are conceivable for vertebrate animals of different kinds, comprising mammals including man, fishes etc. In order to reduce the tendency for arisal of deceases in for example fish cultivated under controlled conditions the compositions according to the present invention may advantageously be supplied to the fish milieu, either directly in the water where cultivation is carried out or as an additive to the food. The invention is particularly useful in connection with cultivation of noble fish, such as salmon, trout or similar species.

The invention will in the following be further described by specific examples. The description is made in connection with the appended drawing, wherein FIG. 1 shows in the form of columns stimulatory index for some plastic surfaces;

FIG. 2 shows introduction of L-929 cells in co-cultivation with macrophages grown on different plastic surfaces.

BIOLOGICAL METHOLOGY

Macrophage cultures

Peritoneal cells from hybrid $C_3D_2$ (C3H/Tifx-×DBA/2) mice ($7 \times 10^5$ cells/well) were transferred onto covering glasses (diameter 14 mm) of circular wells in Costar tissue culture plates (Costar, Cambridge, Mass. USA). After two hours in culture cells which had not adhered to the bottom of the well were washed off. The cells were cultured in Eagle's medium with Earle's salts (DME) (Gibco Biocult Ltd. 3 Washington Road, Paisley, Scotland) in 5% v/v $CO_2$ in air at 37° C. with or without addition of serum. All media contained penicillin (100 I.U./ml) and streptomycin (100 µg/ml).

Scanning electron microscopy (SEM)

Macrophage cultures were fixed in 2.5% glutaraldehyde (Merck) in 0.1M cacodylat buffer pH 7.3 and 0.1M sucrose. The cells were dehydrated in increasing concentrations of ethanol critical point dried in (Hitachi, CPI, Tokyo, Japan) carbon dioxide. The preparations were mounted, covered with gold (Polaron SEM Coating Unit E 5000) and analyzed in a Hitachi SEM (HHS12R) with 20 kV and a tilt angle of 15°. The pictures were taken on Kodak tri-X pan (TX P-120) film.

Animals

In the experiments using B16 melanoma inbred $C_{57}BL$ mice were used. In the rest of the studies the macrophages were obtained from hybrid $C_3D_2$ (C3H Tif×DBA/2) mice. All animals were obtained from Gl. Bomholtgård Ltd. Ry, Denmark.

CHEMICAL METHOLOGY

Curdlan was obtained from Wako Pure Chemical Industries, Osaka, Japan, amylosetype III from Sigma, St. Louis, USA, laminaran from United Stated Biochemical Corp., Cleveland, USA, polymeric aminocompounds Polymin SN® and Polymin P® from Ludwigshafen, West Germany. Aminated polystyrene spheres were obtained from Uglestad, Norway and aminated plates from Falcon. The other chemicals were obtained from Merck, Darmstadt, West Germany.

Sugar analysis

Substances containing the relevant carbohydrates (10 mg) were treated together with internal standard (myo-inositol, 1 mg) with trifluoro acetic acid (0.5M, 2 ml) for 12 hours at 100° C., neutralized ($BaCO_3$) filtered and reduced ($NaBH_4$, 10 mg). After 2 hours pH was adjusted to about 5 using an acid ion exchange (Dowex 50) and the sample was filtrated and evaporated into dryness together with methanol. The sample was acetylated using acetic acid anhydride (1 ml) and pyridine (1 ml) for 15 minutes and at 100° C. The sample was evaporated into dryness and analysed by gas chromatography.

EXAMPLE 1

Modification of Glucans by Introducing Aldehyde Function

Curdlan, which is a water-insoluble $\beta$-1.3-bound D-glucan was degraded in forming acid (90% aq) at 90° C. for 20 minutes according to K. Ogawa, I. Tsurugi and T. Natanabe, The dependence of the conformation of a $(1\rightarrow3)$-$\beta$-D-glucan on chain length in alkaline solution, Carbohydr. Res. 29 (1973) 397. The partially degraded curdlan was then separated into a water-soluble and a water-insoluble fraction. The water-soluble fraction was reduced using sodium borohydride (10 mg/g) in aqueous solution, dialyzed and freeze-dried.

The water-soluble curdlan fraction, laminaran (a water-soluble $\beta$-1.3-bound D-glucan), and amylose (a water-soluble $\alpha$-1.4-bound D-glucan) were alkylated according to S. Hakomori, A rapid permethylation of glucolipid and polysaccharide catalyzed by methylsulfinyl carbanion in dimethylsulfoxide, J. Biochem., (Tokyo) 55 (1964) 205. The polysaccharide (0.5 g) was dissolved in dry dimethylsulfoxide (20 ml) in a serum bottle under nitrogen gas. Using an injection syringe 2M sodiummethylsulfinylmethanide (8 ml) were added. After agitation in an ultrasonic bath at 50° C. for 30 minutes the reaction mixture was allowed to stand at room temperature over night. 2-chloracetaldehydedimethylacetal (5 ml) was added gradually using a syringe. After agitation in the ultrasonic bath at 50° C. for 60 minutes the reaction mixture was poured into water and dialyzed against distilled water. Freeze-drying yielded about 0.45 g of glucan substituted with O-(2.2'-dimethoxyethyl)-groups. The degree of substitution was determined by $^1$H-n.m.r. The first step of the reaction is illustrated below.

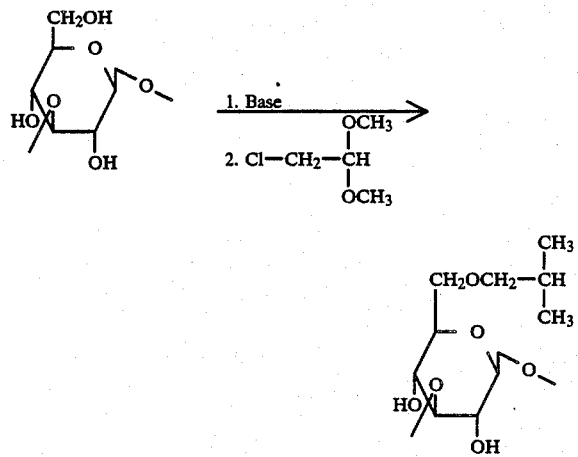

Amylose, partially degraded curdlan and laminaran had on average 0.7, 0.5 and 0.4 O-(2.2$^1$-dimethoxyethyl)- groups, respectively, on each monomer glucose entity. H-n.m.r. spectra were run at 90 MHz in D₂O at 85° C. in a Jeol FX 90 Q n.m.r. instrument.

The O-(2.2¹-dimethoxyethyl)substituted glucan (0.4 g) was treated with hydrochloric acid (25 ml, 0.05M) at 100° C. for 20 minutes, neutralized (0.5M NaOH), dialyzed against distilled water and freeze-dried. The yield was 0.35 g polysaccharide substituted with aldehyde groups. The second step of the reaction can be illustrated as follows:

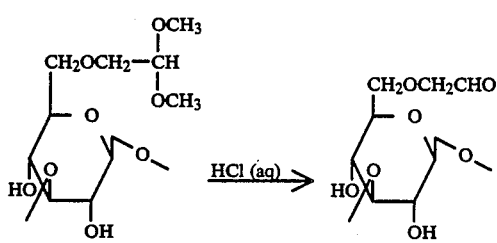

EXAMPLE 2

Modification of Glucans by Introducing an Epoxy-Function

Laminaran (5 g) was dissolved in 60 ml distilled water. Epichlorohydrin (10 ml), 2M sodiumhydroxide solution aq (30 ml) and sodiumborohydride (200 mg) were added. The mixture was allowed to stand under stirring at room temperature over night, dialyzed against acetic acid (10%, 1 liter) and distilled water (5 l) evaporated to a smaller volume (50 ml) and freeze-dried. The yield of epoxy-activated laminaran 4.5 g. The reaction is illustrated below:

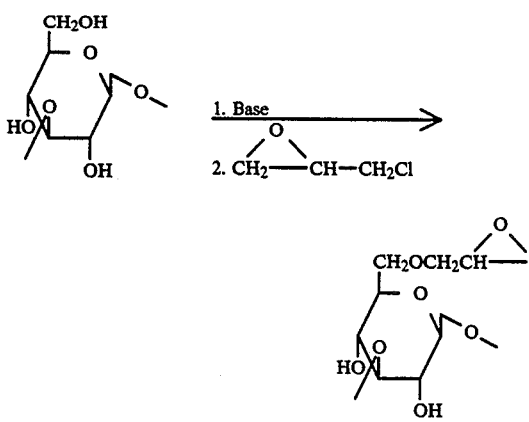

EXAMPLE 3

Periodate Oxidation of Amylose

Amylose is a linear α-1.4-bound D-glucan which is oxidized by periodate (NaIO₄) as follows. Amylose (16.2 g) is dissolved in water (200 ml) and then a solution of NaIO₄ (2.0 g) in water (50 ml) is added. The solution thus obtained is allowed to stand over night under stirring. The material is dialyzed and freeze-dried. Yield 14.5 g. The reaction is illustrated below:

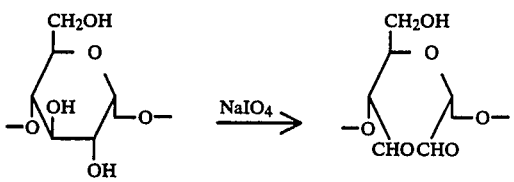

EXAMPLE 4

Sulfatization of Amylose

Amylose (0.5 g) is dissolved in dimethylsulfoxide (4 ml). A sulfurtrioxide-pyridine complex (3 g) is added and the mixture is stirred at 40° C. for 60 minutes. Crushed ice is added (10 g) and water (5 ml). The mixture is then neutralized to pH 7 using sodiumhydroxide (2M). The produce is precipitated in ethanol, dialyzed and freeze-dried. Yield 0.4 g.

EXAMPLE 5

Modification of Plastic Surfaces

An aqueous solution of Polymin SN® (0.005%, w/w) and periodateoxidized amylose (0.5%, w/w) prepared as in example 3 are adjusted to pH 9 (1M NaOH) and added to each well in a plate for tissue cultivation. The wells are washed with distilled water, and an aqueous solution of amylose sulfate (0.02%, w/w, pH 3) prepared as in Example 4 is added at 50° C. After 5 minutes the wells are washed with water. The procedure is repeated twice, and after the last addition of amylose sulfate there is added a 0.01% aqueous solution of Polymin SN® at pH 3. After 5 minutes the wells are washed with distilled water.

EXAMPLE 6

Coupling of Aldehydoglucan According to Example 1 to Plate for Tissue Cultivation Modified According to Example 5

Glucan (4 mg) substituted with aldehyde groups, prepared as per Example 1 is dissolved in 2 ml of phosphate buffer (ph 7.0, 0.2M). To each well of the plate for tissue cultivation according to Example 5 there is added the glucan solution (0.1 ml, 0.1M), phosphate buffer (2.6 ml, pH 7.0) and sodiumcyanoborohydride (100 μg). The plates are allowed to stand at room temperature over night, are washed with distilled water and dried at room temperature. Sugar analysis showed that 0.01 mg glucan had been bound to each well. The coupling sequence is diagramatically shown below:

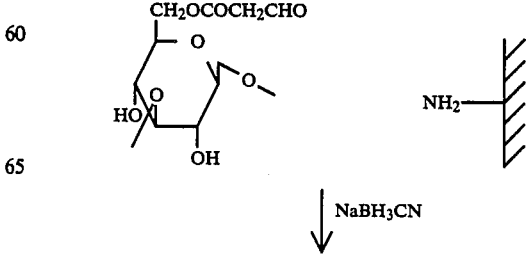

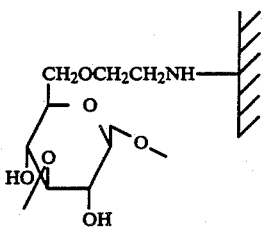

EXAMPLE 7

Coupling of Aldehydoglucan According to Example 1 to Aminated Polystyrene Plates Glucan (4 mg) substituted with aldehyde groups according to Example 1 is coupled to the wells of commercially aminated polystyrene plates for tissue cultivation according to Example 6. (Falcon ® 3847 PRIMARIA CULTURE PLATES). Sugar analysis showed that ~0.005 mg glucan was bound to each well.

EXAMPLE 8

Coupling of Aldehydoglucan According to Example 1 to Aminated Polymethacrylate Spheres Glucan (4 mg) substituted with aldehyde groups according to Example 1 is dissolved in 25 ml phosphate buffer (pH 7.0, 0.2M). To this solution there are added aminated plastic spheres (0.2 g) having a diameter of 2.4 µm manufactured by copolymerization of 2.3-epoxipropylmethacrylate and ethylenglycoldimethacrylate according to J. Uglestad, P. C. Mörk, K. M. Kaggerud, T. Ellingsen and A. Berge SWELLING OF OLIGOMER-POLYMER PARTICLES. NEW METHODS OF PREPARATION OF EMULSIONS AND POLYMER DISPERSIONS. Adv. Colloid Interface Sci. 13 (1980) 101. In addition there is added sodium-cyanoborohydride (0.005 g). The reaction mixture is shaken at room temperature over night, is filtered on glass filter and washed repeatedly with distilled water. The spheres are airdried at room temperature.

EXAMPLE 9

Coupling of Epoxiglucan According to Example 2 to Plastic Surfaces According to Example 5

A 1% solution of epoxy-activated laminaran prepared as per Example 2 was dissolved in phosphate buffer (0.2M, pH 7.0) and added to each well of a plate for tissue cultivation modified as per Example 5. The plates were allowed to stand at room temperature over night, were washed with distilled water and dried at room temperature. Sugar analysis showed that 0.005 mg glucan had been bound to each well. The reaction for the coupling is illustrated diagramatically below:

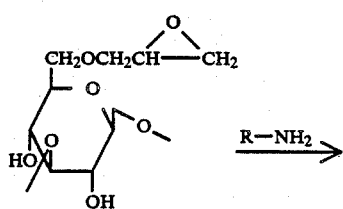

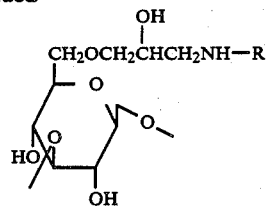

EXAMPLE 10

Stimulation of Macrophages with Surfaces Covered with Immobilized Glucans According to Example 6, 7 and 9

[14]C-labelled D-glucoseamine is added to macrophage cultures in wells of tissue cultivation plates with and without immobilized β-1.3-bound D-glucan. An increased incorporation of D-glucoseamine in glycoproteins in macrophages is an activation parameter for macrophages. After 24 hours the cells are dissolved in 5% trichloroacetic acid and non-incorporated radioactive D-glucoseamine is washed away. The washed cells are dissolved in sodiumhydroxide (1M). When all cell material has been dissolved the solution is transferred to measuring cuvettes and the radioactivity is measured in a scintillation counter. The degree of activation is expressed by the quotient:

$$\text{Stimulation} = \frac{\text{cpm }^{14}\text{C glucoseamine-polysaccharide-stimulated macrophages}}{\text{cpm}^{14}\text{ glucoseamine solely macrophages}}$$

The best results are obtained from plates activated according to Example 6. The results are presented in FIG. 1 which will be explained below.

EXAMPLE 11

Cytostatic Effect of Macrophages Activated on Plates for Tissue Cultivation Covered with β-1.3-Bound D-Glucans Target cells ($2 \times 10^4$ cells/well) were treated with trypsin and added to the macrophages cultures in the presence of glucan-covered plastic surfaces according to Example 6, 7 and 9. After different times there were added 0.5 µCi/ml radioactive thymidine (methyl—[3]H, New England Nuclear, Dreieich, West Germany) to the cultures. Incorporation was measured after an incubation period of 24 hours. After harvesting the cultures the high-molecular material was precipitated with 1M perchloric acid and thoroughly washed before dissolution in 1M sodiumhydroxide solution. The dissolved material was transferred to measuring cells and analyzed in a scintillation counter (Packard Instruments, International, Zürich, Switzerland). The best results were obtained from plates modified according to Example 6. The others gave acceptable results. The results are shown in FIG. 2 which is explained below.

EXAMPLE 12

Experiments Relating to Antibacterial Effect

For investigating the antibacterial effect in vivo $10^6$ virulent pneumococci were injected interperitoneally on mice which had been pretreated with either β-1.3-bound glucancovered polymethacrylate spheres according to Example 8 or saline. In the saline group (4 animals) all mice became sick after 24 hours and died after 48 hours, whereas in the glucan-treated group (8 animals) none of the animals showed any visible symptoms of disease and none of them had died one week later.

The experiment was repeated while injecting virulent *Streptococcus Viridans* and with polymethacrylate spheres treated with β-1.3-bound D-glucans, and the animals showed no signs of disease. The experiments have been repeated three times with the same result.

The degree of stimulation of macrophages determined by morphology (SEM) introduction of $^{14}C$-glucoseamine and by cytostatic effect on target cells of the type L-929.

Macrophages grown on aminated plastic (microtiterplate according to Example 5) or plastic with immobilized amylose incorporated somewhat more $^{14}C$-glucoseamine than cells grown on untreated plastic. However, a ten-fold increase in incorporation of $^{14}C$-glucoseamine was obtained when macrophages were grown on surfaces containing immobilized laminaran or curdlan. This fact is clear from appended FIG. 1 showing the introduction of radioactive $^{14}C$-glucoseamine in macrophages cultivated for 48 hours on microtiterplates of modified plastic. In FIG. 1 stimulatory index relates to introduction (cpm) in stimulated macrophages divided by introduction in normal unstimulated macrophages.

In the Fig. column 1 relates to aminated plastic, column 2 relates to plastic with immobilized amylose, whereas columns 3 and 4 relate to plastic with immobilized curdlan and immobilized laminaran, respectively, where coupling of the glucan is carried out according to Example 5. The results in the figure relate to average±-standard deviation.

As is clear from FIG. 1 using the technique of the present invention relates in a substantial increase of the stimulation of the macrophages.

The cytostatic effect of macrophages was studied by measuring the introduction of radioactive $^3H$-thymidine in L-929-cells with co-cultivation. Unstimulated macrophages have a certain cytostatic effect on L-929-cells, and in a typical experiment cultivation of solely L-929-cells incorporated about 55000 cpm. In the presence of unstimulated macrophages a corresponding cultivation of L-929-cells incorporated about 15000 cpm. 100% in FIG. 2 L-929-cells in co-cultivation with macrophages on aminated plastic incorporated about 50% less of $^3H$-thymidine than L-929-cells in co-cultivation using unstipulated macrophages. This is illustrated in appended FIG. 2, wherein the introduction of radioactive thymidine is shown for a number of cultures of L-929-cells with macrophages. Column 1 shows cultivation in plates of unmodified plastic, column 2 shows the corresponding cultivation carried out in plates of aminated plastic, whereas columns 3, 4 and 5 show cultivation performed in plates of plastic with immobilized amylose, curdlan and laminaran, respectively. Application of the technique according to the invention obviously results in a drastically growth-inhibiting effect by the stimulation provided by the macrophages.

We claim:

1. Macrophage-stimulatory composition containing a water-soluble β-1.3-bound glucan and a water-insoluble carrier to which the glucan has been immobilized.

2. Composition according to claim 1, wherein the glucan is selected from the group consisting of laminaran, curdlan, pachyman, yeast glucan and lichenan.

3. Composition according to claim 1, wherein the glucan is curdlan or laminaran.

4. Composition according to claim 1 wherein the glucan is covalently coupled to the carrier.

5. Composition according to claim 1, wherein the carrier consists of a plastic, an aminated gel or a protein.

6. Composition according to claim 2, wherein the glucan is curdlan or laminaran.

7. Composition according to claim 3, characterized thereby that the carrier contains amino groups to which the glucan is coupled.

8. A process for the manufacture of a composition according to claim 1, said process comprising degrading and thereby dissolving an insoluble β-1.3-bound glucan in an acid, treating said glucan with 2-chloracetaldehydedimethylacetal to achieve substitution with the O-(2,2'-dimethoxyethyl) group, treating said substituted glucan with acid to form an aldehyde substitution, and contacting said aldehyde-substituted glucan with a carrier containing amino groups in the presence of cyanoborohydride to achieve covalent coupling to the carrier.

* * * * *